United States Patent
Patterson et al.

[11] Patent Number: 5,944,686
[45] Date of Patent: Aug. 31, 1999

[54] INSTRUMENT FOR CREATING A FLUID JET

[75] Inventors: Frank Van Patterson, Exeter, N.H.; Marvel John Yoder, Andover; Timothy E. Moutafis, Gloucester, both of Mass.

[73] Assignee: HydroCision, Inc., Wilmington, Mass.

[21] Appl. No.: 08/481,566

[22] Filed: Jun. 7, 1995

[51] Int. Cl.$^6$ .................................................. A61B 17/20
[52] U.S. Cl. ............................................ 604/22; 606/159
[58] Field of Search .............................. 604/22; 606/159, 606/167, 127–128, 170; 134/166 C, 167 C, 168 C

[56] References Cited

U.S. PATENT DOCUMENTS

| | | |
|---|---|---|
| 3,818,913 | 6/1974 | Wallach . |
| 3,930,505 | 1/1976 | Wallach . |
| 4,111,490 | 9/1978 | Liesveld . |

(List continued on next page.)

FOREIGN PATENT DOCUMENTS

| | | |
|---|---|---|
| 0 485133 A1 | 5/1992 | European Pat. Off. . |
| 0 489496 A1 | 6/1992 | European Pat. Off. . |
| 0 551920 A1 | 1/1993 | European Pat. Off. . |
| 225 618 A1 | 8/1985 | German Dem. Rep. . |
| 3421 390 A1 | 12/1985 | Germany . |
| 42 01 992 A1 | 7/1993 | Germany . |
| WO 94/14584 | 12/1993 | WIPO . |

OTHER PUBLICATIONS

Baer H.U. Maddern G.J. Blumgart L.H.: A new water jet dissector—initial experience in hepatic surgery, Br.J. Surg. 1991: 78:502–503.

Baer H.U., Maddern G.J., Blumgart L.H.: Hepatic surgery faciliated by a new jet dissector, HPB Surgery 1991; 4:137–146.

Baer H.U., Maddern G.J., Dennison A.R., Blumgart L.H.: Water–jet dissection in hepatic surgery, Invasive Therapy 1992; 1:169–172.

Baer H.U., Dennison A.R., Maddern G.J., Blumgart L.H.: Subtotal hepatectomy: a new procedure based on the inferior right hepatic vein. Br. J. Surg. 1991; 78:1221–1222.

Baer H.U., Blumgart L.H.: Anmerkungen zur Veroffentlichung von H.G. Rau et al.; Schneiden mit dem Wasserstrahl (Jetting Cutting)—eine Alternative zum Ultraschallaspirator? [Chirurg 1990; 61:7351] Chirurg 1991;62:356.

Terzis, A.J.A. et al., A New System for Cutting Brain Tissue Preserving Vessels: water jet cutting., Br.J. Neur. 1989, 3:361–66.

Giraud J–Y, et al., Bone Cutting. Clin. Phys. Meas. 1991, 12:1–19.

Field, J.E., The physics of liquid impact, shock wave interactions with cavities, and the implications to shock wave lithotripsy. Phys. Med. Biol. 1991, 11:1475–84.

Zhong P. et al., Propagation of shock waves in elastic solids caused by cavitation microjet impact. II: Application in extracorporeal shock wave lithotripsy. J. Acoust. Soc. Am. 1993, 94:29–36.

Izumi R. et al., Hepatic Resection Using a Water Jet Dissector. Jpn. J. Surg. 1993, 23:31–35.

*Primary Examiner*—Wynn Wood Coggins
*Assistant Examiner*—Deborah Blyveis
*Attorney, Agent, or Firm*—Wolf, Greenfield & Sacks, P.C.

[57] ABSTRACT

An instrument for delivering a variable pressure stream of fluid as a coherent jet. The instrument may be configured for holding in the hand of a user or for manipulation by machine control. The orifices may be oriented axially, transversely or obliquely. A deflector may be provided opposite the orifice to transform the jet stream into a harmless spray. The deflector may be slidable (in the axial mode) or pivotable (in the transverse mode) to ensure a small instrument profile. The instrument may be moldable allowing the user to reshape the jet tip into a desired configuration. The instrument may be remotely steerable and enable a user to selectively alter the direction of the jet without having to remove the instrument from the surgical site.

29 Claims, 5 Drawing Sheets

U.S. PATENT DOCUMENTS

| | | |
|---|---|---|
| 4,465,438 | 8/1984 | Bräuer et al. . |
| 4,560,373 | 12/1985 | Sugino . |
| 4,690,672 | 9/1987 | Veltrup . |
| 4,761,039 | 8/1988 | Hilaris . |
| 4,776,769 | 10/1988 | Hilaris . |
| 4,795,217 | 1/1989 | Hilaris . |
| 4,798,339 | 1/1989 | Sugino et al. . |
| 4,811,902 | 3/1989 | Nagata . |
| 4,827,679 | 5/1989 | Earle, III . |
| 4,898,574 | 2/1990 | Uchivama et al. . |
| 4,913,698 | 4/1990 | Ito et al. . |
| 4,937,985 | 7/1990 | Boers . |
| 4,950,238 | 8/1990 | Sullivan . |
| 5,018,670 | 5/1991 | Chalmers . |
| 5,037,431 | 8/1991 | Summers . |
| 5,052,624 | 10/1991 | Boers . |
| 5,057,098 | 10/1991 | Zelman . |
| 5,074,862 | 12/1991 | Rausis . |
| 5,092,744 | 3/1992 | Boers . |
| 5,125,582 | 6/1992 | Surjaatmadja et al. . |
| 5,133,687 | 7/1992 | Malloy . |
| 5,135,482 | 8/1992 | Neracher . |
| 5,162,016 | 11/1992 | Malloy . |
| 5,205,779 | 4/1993 | O'Brien et al. . |
| 5,217,465 | 6/1993 | Steppe . |
| 5,242,449 | 9/1993 | Zaleski . |
| 5,314,375 | 5/1994 | O'Brien et al. . |
| 5,322,504 | 6/1994 | Doherty . |
| 5,370,609 | 12/1994 | Drasler et al. . |
| 5,527,330 | 6/1996 | Tovey . |
| 5,527,331 | 6/1996 | Kresch et al. . |
| 5,536,242 | 7/1996 | Willard et al. . |
| 5,562,640 | 10/1996 | McCabe et al. . |
| 5,697,281 | 12/1997 | Eggers et al. . |
| 5,709,697 | 1/1998 | Ratcliff et al. . |

INSTRUMENT FOR CREATING A FLUID JET

FIELD OF THE INVENTION

The invention relates to an instrument for creating a fluid jet.

BACKGROUND OF THE INVENTION

Systems are known which employ a nozzle or handpiece having a small diameter orifice to generate a jet stream as a high pressure fluid flows therethrough. Instruments specifically for use in surgical applications also have been proposed. U.S. Pat. No. 3,930,505 discloses a variable pressure jet for disintegrating eye lens tissue. A system for use in hepato-biliary surgery, known as the Hepatom, has been reported in the literature and may be available outside the United States. U.S. Pat. No. 5,370,609, and related European patent applications 0 485 133 and 0 489 496, describe a water jet catheter which delivers a high pressure liquid stream to dislodge, emulsify and remove deposits from a vein or artery.

SUMMARY OF THE INVENTION

The present invention is an instrument for delivering a variable pressure stream of fluid as a coherent jet. The instrument may be configured for holding in the hand of a user or for manipulation by machine control, such as an X/Y/Z positioner. The instrument includes an elongated body having a lumen communicable with a source of pressurized fluid that terminates in one or more fine axial or transverse jet orifice(s) having a diameter in the range of tenths of millimeters, preferably 0.1 millimeter. The jet orifices may be oriented axially, transversely or obliquely. A hair-thin cutting beam is formed as the fluid stream spews through the tiny jet orifice at pressures as high as 50,000 p.s.i. For the purposes of this application, the term "fluid jet cutting" is intended to broadly include the use of a high pressure fluid stream to cut, drill, bore, perforate, strip, delaminate, liquefy, ablate, shape and other forming and machining operations. A hand tightenable connector may be provided at a proximal end of the instrument to ensure a leaktight seal with a delivery tube that conducts the fluid under pressure into the instrument.

Various configurations of the jet creating instrument tip may be employed. Preferably, the tip is selectively moldable allowing the user to reshape or bend the jet tip into a configuration, or at an angle, which facilitates positioning at the cutting site. This feature is especially attractive where the locus of cutting is difficult to reach. A deflector or catcher may be provided opposite the orifice to transform the liquid jet into a harmless spray, preventing the fluid arc from cutting deeper than is desired or from attacking surrounding areas if the stream becomes misdirected. To ensure a small instrument profile, the catcher may be slidable (in the axial mode) or pivotable (in the transverse mode) from a slender configuration employed during insertion of the instrument to an expanded configuration at the cutting site. Alternatively, one or more jets may be oriented to create a deflecting spray that accomplishes the same aim as the catcher. A separate outlet may be provided on the jet forming instrument which is communicable at a proximal end with a source of suction to allow aspiration of debris caused by the fluid cutting and the cutting medium. Alternatively, a separate suction line may be employed.

The jet instrument is particularly suitable for use in surgical procedures. Selective variation of the jet stream pressure, between 1 and 50,000 p.s.i., allows the surgeon to cut hard bone, soft bone, cartilage and tissue, to strip away tissue exposing underlying organs or vessels or, simply, to wash away blood and debris created by the surgical procedure. The latter irrigating function ensures good visibility of the operative site. Preferably, the jet is a fine, coherent steam of sterile cutting solution, such as physiological saline or, perhaps, a liquefied gas such as carbon dioxide, which cuts or ablates the tissue or bone, and the stream may then be used to pulverize the biological fragments into smaller pieces. The emulsified debris may be flushed or evacuated from the surgical site. The jet wand may include a suction nozzle or a separate suction line may be employed. Alternatively, positive pressure evacuation may be employed to remove the effluent.

Selective variation of the jet pressure allows the surgeon to target precisely a visible low pressure stream on the portion of the bone or tissue to be excised and then to cut the bone or tissue with the already pin-pointed jet simply by increasing the jet to a higher, cutting pressure. A physiologically inert dye may be dispersed in the sterile cutting fluid to enhance focusing of the low pressure stream. Even when fully submersed in fluid, the jet is ascertainable by the cavitation within the surrounding solution. The hair-thin fluid beam, having a diameter in the tenths of millimeters and, preferably, in the range from 20–500 microns, permits the surgeon to make fine controlled incisions without damaging neighboring tissue, organs, vessels or nerves.

A slender, hand-holdable wand or nozzle is preferred for surgical applications, facilitating use of the fluid jet cutting system in procedures which present narrow spaces and complicated geometries. The reduced configuration suggests use of the instrument in arthroscopy and other procedures where small openings and cannulas may be used to enter the operative field. Alternatively, the jet forming instrument may embody a tip at the distal end of a burst resistant catheter, such as is disclosed in U.S. Pat. No. 5,370,609, the contents of which are incorporated herein by reference.

It is an object of the present invention to provide a jet creating instrument with a controlled length cutting beam.

It is an additional object of the present invention to provide a jet forming instrument with a slender profile.

It is a still further object of the present invention to provide a jet instrument with a tip that is remotely manipulable.

Other objects and features of the advantages of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The forgoing and other objects and advantages of the invention will be appreciated more fully from the following drawings in which.

DESCRIPTION OF THE PREFERRED EMBODIMENTS

Figure 1:
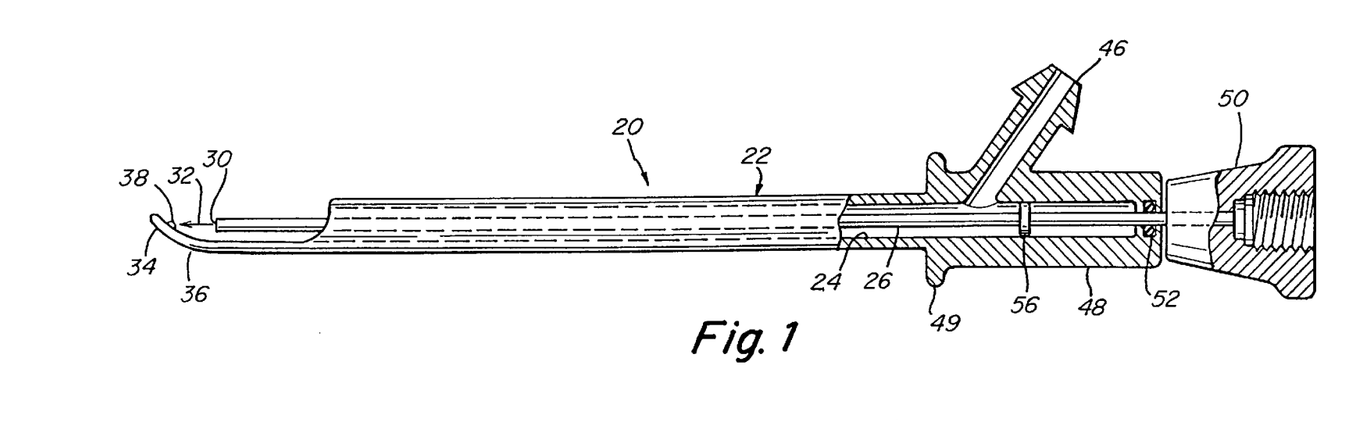
FIGS. 1 and 2 illustrate a jet wand with an axially moveable delivery tube for varying the length of the fluid jet.
Figure 2:
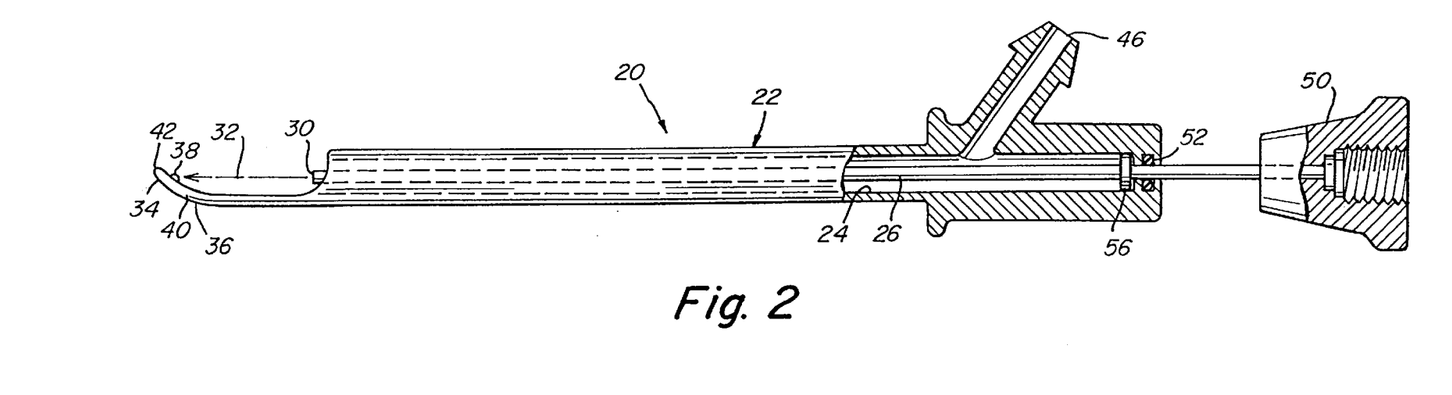

A jet instrument 20, illustrated in FIGS. 1 and 2, includes an elongated body 22 having a central lumen 24 and a displaceable fluid delivery line 26 extending therethrough. The delivery line is constructed of burst resistant hypotube, such as 14XT gauge type 304 or 316 stainless steel, which is rated for pressures in excess of 50,000 p.s.i. An axially facing jet at the distal tip 30 of the delivery line creates a fine beam of high pressure fluid 32. A distal tip 34 of a catcher or deflector 36 curves upwardly from the elongated body into the path of the fluid jet, diffusing the liquid beam into a harmless spray. The deflector may include a wear resistant surface, such as the illustrated ball bearing 38, to increase the working life of the instrument. Modification of the instrument to form an electro-cautery device is contemplated. The deflector may have a sharpened edge and tip 40, 42, respectively, allowing the surgeon to create an incision with the instrument. Also, a pointed tip may be employed to pierce and hold an article while it is being cut.

A side port 46 extends from the main body and may be placed in communication with a source of suction to draw debris and effluent away from the surgical site. Alternatively, the port may be connected to a source of medication or irrigation. It also is contemplated to provide additional side ports if required by a specific application.

Retracting a handle 50 draws the jet away from the catcher, allowing the user to selectively vary the size of the cutting beam. Where the bone, cartilage or tissue being removed is large, the jet will be more proximally disposed to increase the length of the liquid arc. A distal positioning may be appropriate where a small target is presented. A seal 52 is provided in the proximal end of the body, around the hypotube, preventing leakage of the fluid yet permitting axial movement of the delivery line. A limit washer 56, secured to the delivery tube, is halted by a stop in the proximal end of the body, preventing further retraction of the delivery tube. The washer may be positioned to prevent the jet opening from being withdrawn into the body lumen, if desired. The handle, a contoured surface of the instrument body 48 including an annular rim 49 facilitate relative movement of the delivery tube and body by a user.

Figure 3:
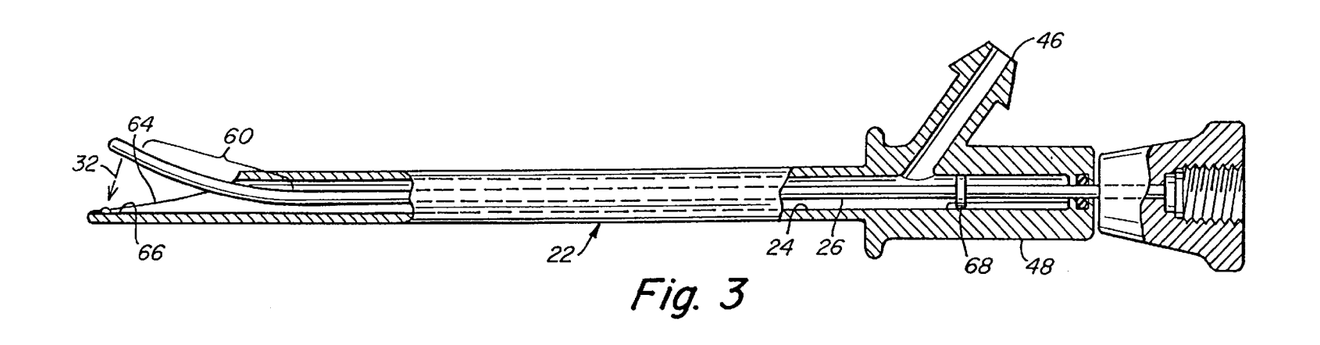
FIGS. 3 and 4 show a jet wand with a displaceable transverse jet.
Figures 4, 5:
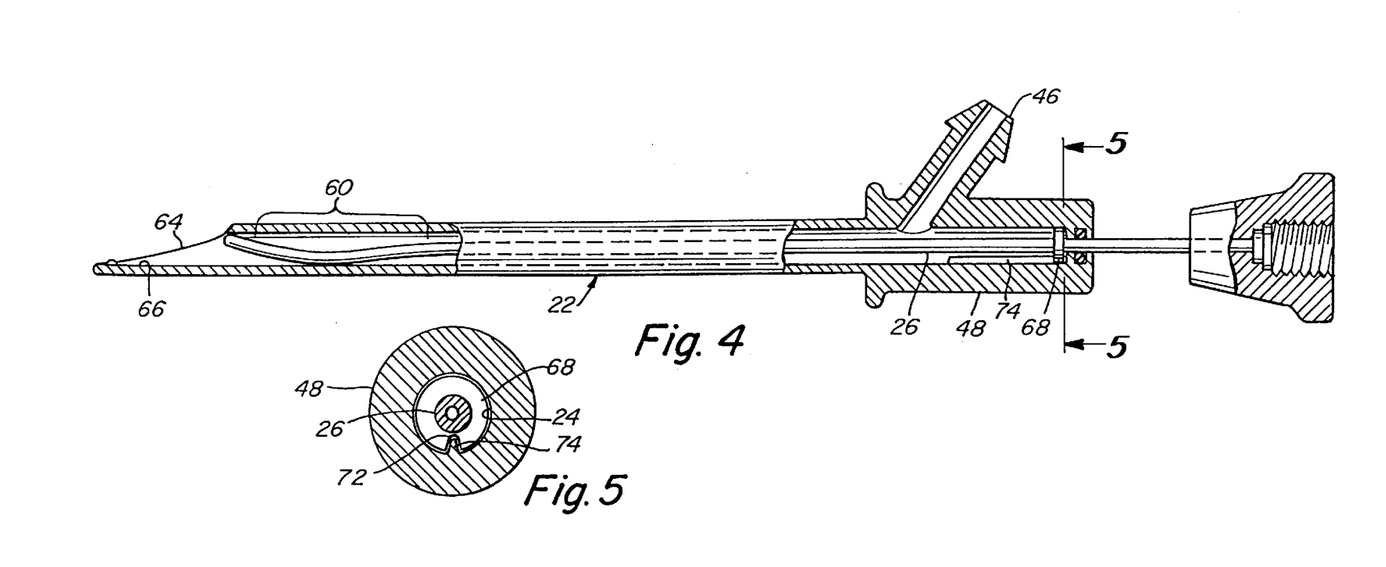
FIG. 5 illustrates a stabilizing mechanism for preventing rotation of the delivery line in the wand shown in FIG. 4 as seen from line 5—5.

An instrument with a transverse jet is illustrated in FIGS. 3–5. The tip of the delivery tube is pre-shaped with an outward curve 60, allowing the user to selectively vary the length of the cutting beam by incrementally retracting the delivery tube into the body lumen. A fully retracted delivery tube, as shown in FIG. 4, provides a reduced profile compatible with placement of the instrument, particularly through narrow passages. The distal tip, preferably, is resilient, assuming a straight configuration when seated in the body lumen but springing back to an outwardly curved shape upon deployment. A portion 64 of the distal segment of the main body is exposed, permitting expansion of the jet tip. The deflector is provided on an axial extending face 66 opposite of the transverse jet. To prevent rotation of the delivery line, an alignment washer 68 having a groove 72 is mated with a positioning rail 74 in the body. The groove and rail arrangement permits axial movement of the delivery line but prevents rotation which could, detrimentally, lead to a misdirected spray beyond the protection of the deflector.

Figure 6:
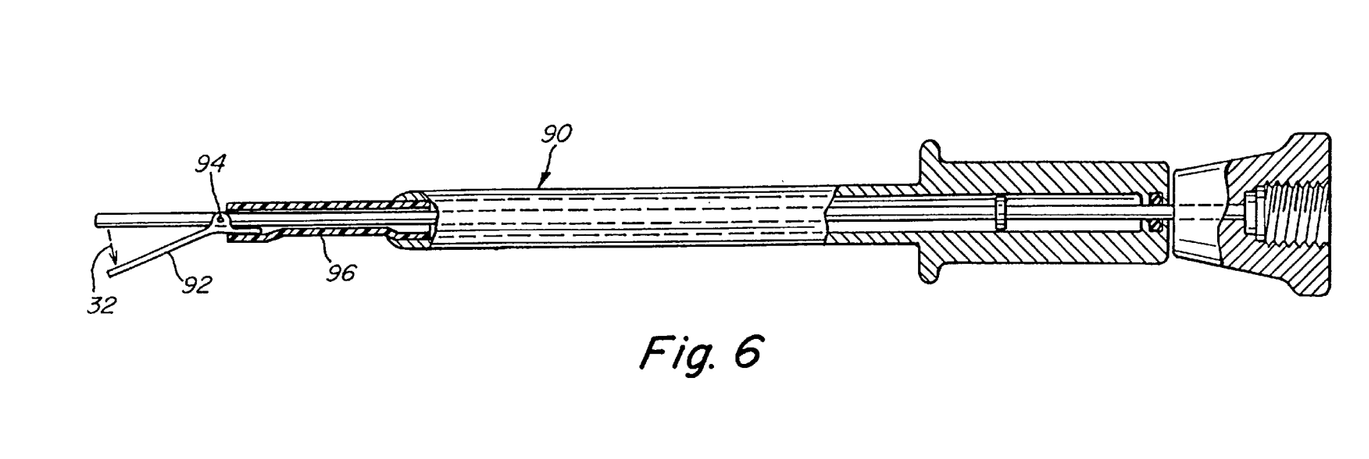
FIGS. 6 and 7 illustrate a transverse jet wand with a pivoting deflector.
Figure 7:
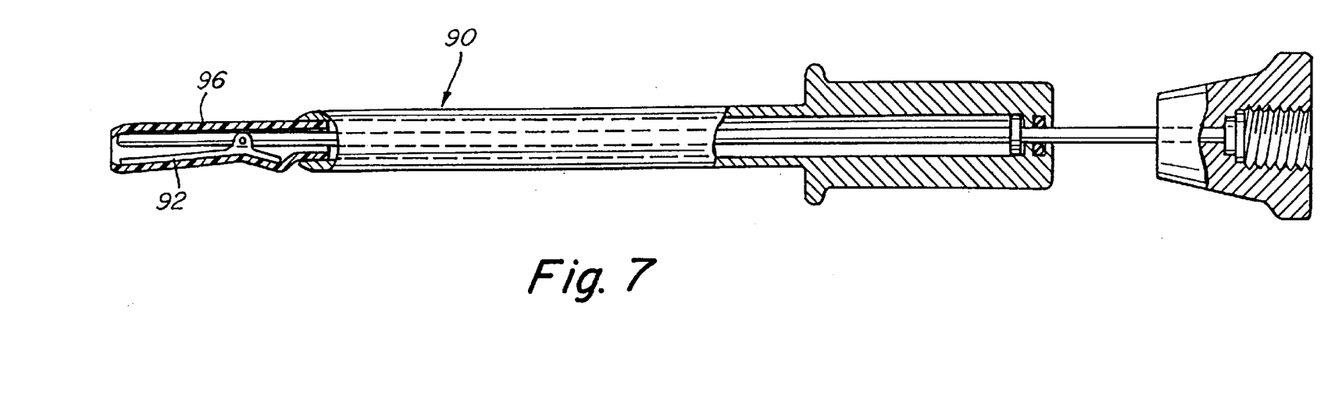

An instrument 90 with a pivoting deflector 92 is illustrated in FIGS. 6 and 7. A deflector is mounted on the distal end of the delivery tube by pins 94 (only one pin is shown). The ends of the defector are angled outward with respect to the delivery tube such that the deflector car rock on the pins. When in a retracted position, shown in FIG. 7, an elastomeric sheath 96 disposed at the distal end of the body, surrounds the deflector and maintains the deflector in a reduced profile. Extension of the deflector out of the sheath beyond the pins causes the deflector to pivot into the open configuration, shown in FIG. 6. When in this configuration, the deflector is able to diffuse a transverse jet stream.

Figure 8:
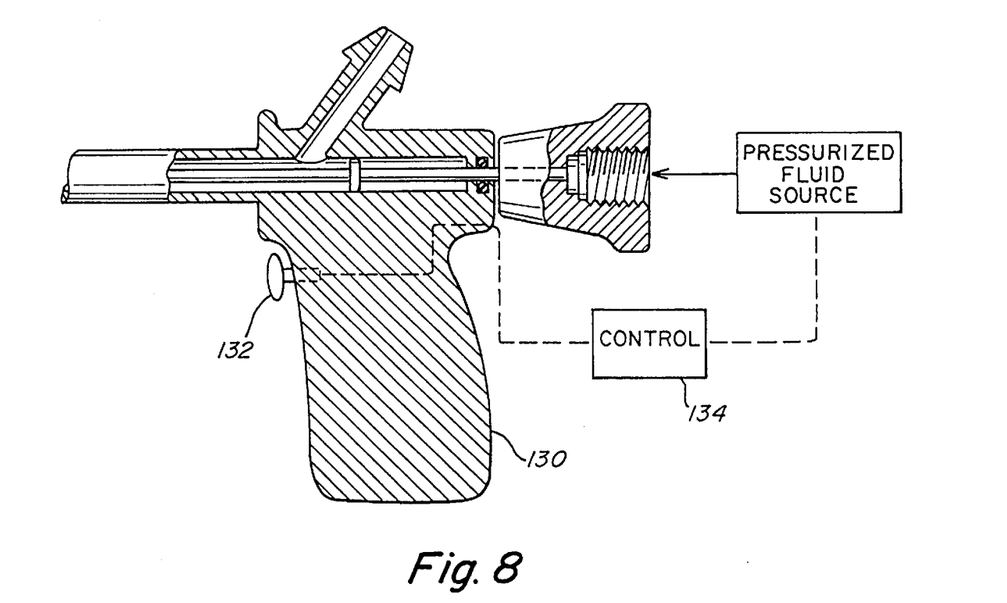
FIG. 8 shows a pistol grip and trigger portion of a jet wand.

FIG. 8 shows the proximal end of a jet wand configured with a pistol grip 130 for easy manipulation by a user. The jet handle may be provided with a trigger 132 which is connectable to a control 134 for varying the pressure of the fluid jet.

Figure 9:
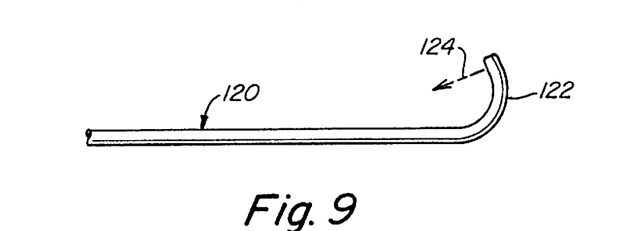
FIGS. 9 and 10 show a jet wand having a formable portion.
Figure 10:
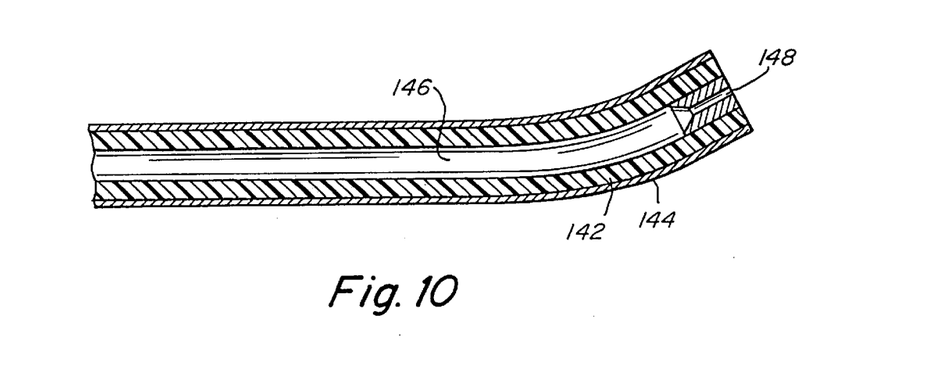

FIGS. 9 and 10 illustrate a jet wand having a moldable tip which facilitates navigation of the instrument around obstructions during positioning of the jet relative to the surgical site. Consequently, a moldable wand has a particular advantage over conventional percutaneous cutting probes, such as burrs and rotary cutters or shavers, which require a drive shaft for rotary motion which is generally incapable of bending without leading to mechanical failure. Because the cutting energy of the fluid jet wand is a pressurized liquid, bends and turns in the delivery line will not detrimentally impede the generation of a cutting force at the distal tip.

The preferred material for forming the delivery tube and body is a thick wall gauged stainless steel which is shapeable without kinking or occluding the high pressure fluid lumen. The components are preferably formed from a malleable alloy or are subject to heat treatment to achieve the requisite kink resistance and flexibility. FIG. 9 shows a delivery tube 120 having a bend 122 at the distal and which can be adapted to direct the jet spray 124 out of line-of-sight. The tip of the instrument may be provided with a greater degree of hardness than a more proximal section, permitting the distal tip to maintain an edge where desired as well as to allow the instrument end to be used as a manipulator of tissue and bone during a procedure.

FIG. 10 illustrates a different arrangement for selectively molding the jet tip. Here, a relatively thick, semi-rigid tube 142 is surrounded by a relatively thin walled flexible metal sheath 144. The tube 142, preferably constructed of a polymeric material, such as nylon, has a lumen 146 adapted to carry the pressurized fluid to the jet opening 148 at the distal end of the wand. The flexible steel imparts moldability to the device.

Figure 11:
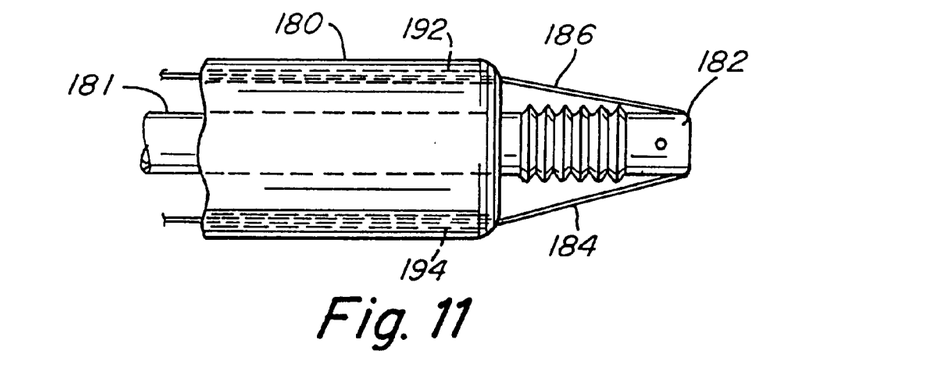
FIGS. 11, 12 and 13 illustrate an instrument for creating a fluid jet having a steerable tip.
Figure 12:
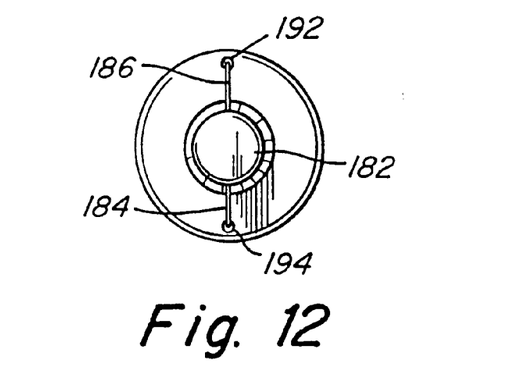
Figure 13:
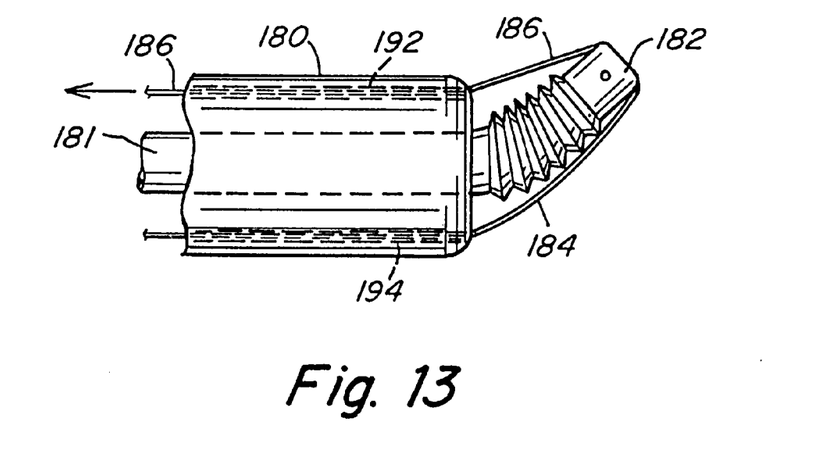

A remotely steerable jet wand is illustrated in FIGS. 11–13, allowing a user to selectively alter the direction of the jet without having to remove the instrument from the surgical site. This instrument is particularly indicated for use where the surgical site is remotely visualized. A main body 180 has a delivery tube 181 extending therethrough. A flexible delivery tube distal tip 182 is fixed at diametrically opposed sides by ends of high tensile wires 184, 186. The control wires extend along the length of the main body, preferably through a pair of parallel lumens 192, 194, shown in FIG. 12. Manipulation of the proximal ends of the wires causes the distal tip to bend accordingly. Selective, real time shaping of the distal tip should facilitate travel of the surgical wand to the cutting site and will allow the surgeon to vary the direction of the fluid cutting jet. FIG. 13 illustrates the distal tip being directed by pulling the wire 186. Although two wires are illustrated, one or more than two wires could be employed as would be apparent to one of skill in the art.

It should be understood that the foregoing description of the invention is intended merely to be illustrative thereof and that other equivalents, embodiments and modifications of the invention may be apparent to those skilled in the art.

What is claimed is:

1. An instrument for creating a fluid jet, comprising:
   a body including a lumen for conducting a high pressure fluid and at least one jet opening, in communication with said lumen, for forming a cutting jet as high pressure fluid streams therethrough; and
   a deflector supported by said body and locatable opposite said at least one jet opening for transforming the cutting jet into a harmless spray;
   wherein said deflector and said at least one jet opening are moveable longitudinally relative to one another.

2. The instrument recited in claim 1 wherein said lumen and said at least one jet opening are included within a delivery tube moveable within a passageway in said body of the instrument.

3. The instrument recited in claim 2 further including a side port extending from said body and in communication with said passageway.

4. The instrument recited in claim 3 wherein said side port is connectable to an evacuation source.

5. The instrument recited in claim 2 wherein a distal tip of said delivery tube has an expanded configuration when deployed from said passageway and a reduced configuration when retracted within said passageway.

6. The instrument recited in claim 5 wherein said expanded configuration includes an outward curve.

7. The instrument recited in 2 wherein a seal is provided in said passageway around said delivery tube to prevent fluid leakage.

8. The instrument recited in claim 1 wherein a distance between said at least one jet opening and said deflector defines a cutting jet length which is varied by relative longitudinal movement of said deflector and said at least one jet opening.

9. The instrument recited in claim 1 further comprising a hand tightenable connector for joining said body to a source of high pressure fluid, said hand tightenable connector being in fluid communication with said lumen.

10. The instrument recited in claim 1 wherein said body is elongated.

11. The instrument recited in claim 1 wherein said deflector is mounted on a distal end of a delivery tube moveable within a passageway in said body of the instrument.

12. The instrument recited in claim 1 wherein said deflector is mounted at a distal tip of said instrument, longitudinally spaced from said at least one jet opening.

13. The instrument recited in claim 1 wherein said body is adapted at a first end thereof for connection with a source of high pressure fluid.

14. An instrument for creating a fluid jet, comprising:
   a body including a lumen for conducting a high pressure fluid and at least one jet opening, in communication with said lumen, for forming a cutting jet as high pressure fluid streams therethrough; and
   a deflector supported by the instrument and spaced from said body and said lumen, for transforming the cutting jet into a harmless spray;
   wherein said deflector and said body are moveable relative to one another.

15. The instrument recited in claim 14 wherein said deflector is mounted on a distal end of a delivery tube moveable within a passageway in said body of the instrument.

16. The instrument recited in claim 15 wherein said lumen and said at least one jet opening are included within said delivery tube.

17. The instrument recited in claim 15 wherein a distal tip of said delivery tube has an expanded configuration when deployed from said passageway and a reduced configuration when retracted within said passageway.

18. The instrument recited in claim 14 wherein said deflector and said one jet opening are moveable relative to one another.

19. The instrument according to claim 18 wherein a distance between said at least one jet opening and said deflector defines a cutting jet length which is varied by relative lateral movement of said deflector and said at least one jet opening.

20. The instrument recited in claim 14 wherein said deflector is moveable relative to said body.

21. The instrument recited in claim 14 wherein said body is moveable relative to said deflector.

22. An instrument for creating a fluid jet, comprising:
   a body including a lumen for conducting a high pressure fluid and at least one jet opening, in communication with said lumen, for forming a cutting jet as high pressure fluid streams therethrough; and
   a deflector supported by said body and locatable opposite said at least one jet opening for transforming the cutting jet into a harmless spray;
   wherein said deflector and said at least one jet opening are moveable laterally relative to one another.

23. The instrument recited in claim 22 wherein said lumen and said at least one jet opening are included within a delivery tube moveable within a passageway in said body of the instrument.

24. The instrument recited in claim 23 wherein a distal tip of said delivery tube has an expanded configuration when deployed from said passageway and a reduced configuration when retracted within said passageway.

25. The instrument recited in claim 22 wherein said deflector and said at least one jet opening are moveable axially relative to one another.

26. The instrument recited in claim 22 wherein said lumen and said at least one jet opening are included with a delivery tube moveable within a passageway in said body of the instrument, said deflector being pivotally mounted to said delivery tube.

27. The instrument recited in claim 22 wherein a distance between said at least one jet opening and said deflector defines a cutting jet length which is varied by relative lateral movement of said deflector and said at least one jet opening.

28. An instrument for creating a fluid jet, comprising:

an elongated body having a passageway extending from an opening at a first end and a fluid delivery line moveable in said passageway, said fluid delivery line having a proximal end larger than said opening at a first end which is adapted for connection with a source of high pressure fluid, said fluid delivery line including at least one jet opening for creating a cutting jet as high pressure fluid streams therethrough, and a deflector for transforming the cutting jet into a harmless spray, said deflector and said at least one jet opening being moveable relative to one another.

29. The instrument as recited in claim 14, wherein a distance between said at least one jet opening and said deflector defines a cutting length, which is varied by relative movement of said deflector and said at least one jet opening.

* * * * *

UNITED STATES PATENT AND TRADEMARK OFFICE
CERTIFICATE OF CORRECTION

PATENT NO. : 5,944,686

DATED : August 31, 1999

INVENTOR(S) : Frank Van Patterson et al.

It is certified that error appears in the above-identified patent and that said Letters Patent is hereby corrected as shown below:

Column 8, line 4, please delete "claim 14" and insert therefor -- claim 28 --.

Signed and Sealed this

First Day of February, 2000

Attest:

Q. TODD DICKINSON

Attesting Officer    Acting Commissioner of Patents and Trademarks